US011135397B2

(12) United States Patent
Hauptmann et al.

(10) Patent No.: US 11,135,397 B2
(45) Date of Patent: Oct. 5, 2021

(54) TWO-DIMENSIONAL ACOUSTIC CR NEUROMODULATION USING FREQUENCY AND PERIODICITY AS CONTROL PARAMETERS

(71) Applicant: Aureliym GmbH, Bad Neuenahr-Ahrweiler (DE)

(72) Inventors: Christian Hauptmann, Starnberg (DE); Mark Williams, London (GB); Markus Haller, Beirut (LB); Sven Jürgen Grob, Düsseldorf (DE)

(73) Assignee: Aureliym GmbH, Bad Neuenahr-Ahrweiler (DE)

( * ) Notice: Subject to any disclaimer, the term of this patent is extended or adjusted under 35 U.S.C. 154(b) by 377 days.

(21) Appl. No.: 16/323,254

(22) PCT Filed: Aug. 4, 2017

(86) PCT No.: PCT/EP2017/000954
§ 371 (c)(1),
(2) Date: Feb. 4, 2019

(87) PCT Pub. No.: WO2018/024374
PCT Pub. Date: Feb. 8, 2018

(65) Prior Publication Data
US 2019/0224442 A1 Jul. 25, 2019

Related U.S. Application Data

(60) Provisional application No. 62/371,149, filed on Aug. 4, 2016.

(51) Int. Cl.
*A61M 21/00* (2006.01)
*A61B 5/12* (2006.01)
*A61F 11/00* (2006.01)

(52) U.S. Cl.
CPC ............ *A61M 21/00* (2013.01); *A61B 5/128* (2013.01); *A61F 11/00* (2013.01);
(Continued)

(58) Field of Classification Search
CPC ...... A61M 21/00–02; A61F 11/00–045; A61B 5/12–128
See application file for complete search history.

(56) References Cited

U.S. PATENT DOCUMENTS

| | | | |
|---|---|---|---|
| 4,222,393 A | 9/1980 | Hocks et al. | |
| 2003/0232098 A1* | 12/2003 | Keate | A61K 2300/00 424/752 |

(Continued)

FOREIGN PATENT DOCUMENTS

WO 2008046882 A2 4/2008

OTHER PUBLICATIONS

International Search Report and Written Opinion issued in International Application No. PCT/EP2017/000954 dated Dec. 8, 2017.

*Primary Examiner* — Thaddeus B Cox
(74) *Attorney, Agent, or Firm* — Quinn IP Law

(57) ABSTRACT

Described and disclosed herein are various embodiments of systems, devices, components and methods configured to deliver a two-dimensional acoustic coordinated reset neuromodulation therapy to a patient's auditory cortex. A novel auditory stimulation regime is employed, where suitably configured therapeutic signals that take into account the patient's tinnitus frequency and periodicity are employed to excite areas surrounding the center of tinnitus excitation in the patient's auditory cortex.

20 Claims, 8 Drawing Sheets

(52) U.S. Cl.
CPC ............... *A61M 2021/0027* (2013.01); *A61M 2205/3303* (2013.01); *A61M 2205/50* (2013.01)

(56) References Cited

U.S. PATENT DOCUMENTS

| | | | |
|---|---|---|---|
| 2010/0317666 A1* | 12/2010 | Christensen | A61K 31/495 514/249 |
| 2011/0071340 A1 | 3/2011 | McGuire | |
| 2015/0003635 A1 | 1/2015 | Baker et al. | |
| 2015/0003650 A1* | 1/2015 | Drexler | A61B 5/4848 381/312 |
| 2015/0051656 A1* | 2/2015 | Kilgard | A61N 1/361 607/3 |

* cited by examiner

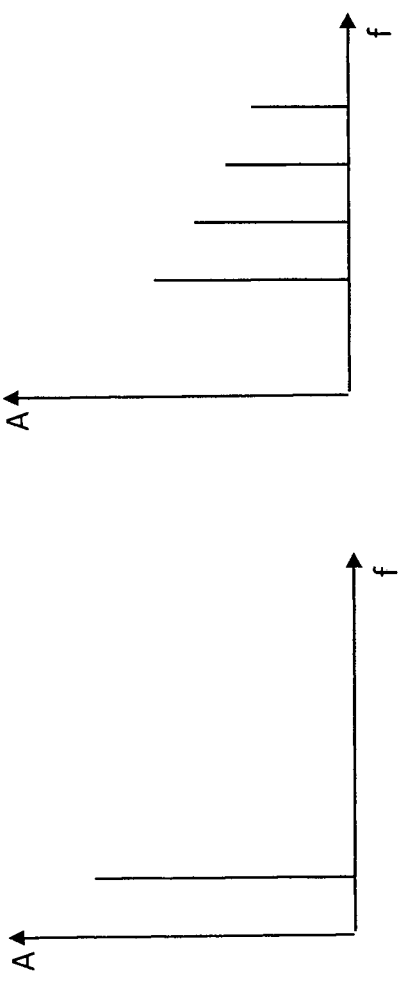
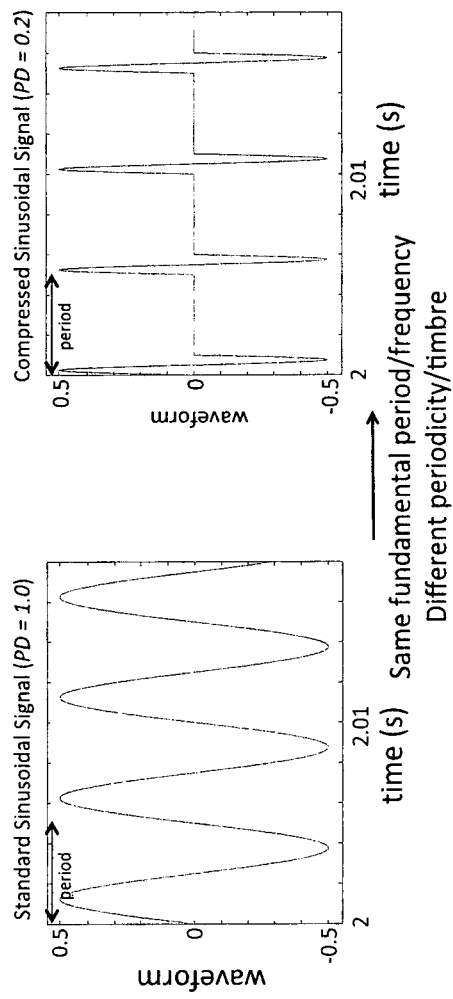
Fig. 2a
Fig. 2b

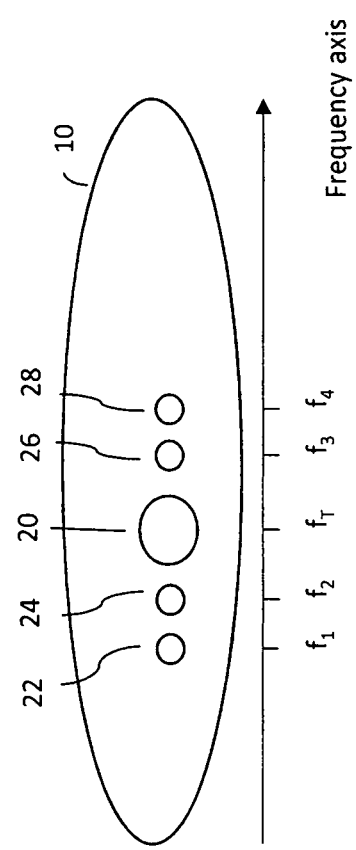
Fig. 3 – Prior Art

TWO-DIMENSIONAL ACOUSTIC CR NEUROMODULATION USING FREQUENCY AND PERIODICITY AS CONTROL PARAMETERS

FIELD OF THE INVENTION

Various embodiments of the systems, devices, components and methods disclosed and described herein relate to acoustic coordinated reset neuromodulation therapies delivered to patients via external and/or implanted systems, devices and components.

BACKGROUND

Acoustic coordinated reset (CR) neuromodulation therapy is a form of noninvasive neuromodulation therapy for treating primary tinnitus, in particular, the frequency-specific, often tonal tinnitus commonly seen in these patients. See, for example, "Counteracting tinnitus by acoustic coordinated reset neuromodulation," Restor. Neurol. Neurosci. 30(2): 137-159. Tass et al., 2012.

Acoustic CR neuromodulation uses acoustic signals that stimulate the auditory neural tracts as they account for hearing level and psychoacoustic characteristics of the tinnitus percept (Tass et al., 2012). These techniques employ well-accepted neuroplasticity principles and were developed using computational modeling. See, for example, "A model of desynchronizing deep brain stimulation with a demand-controlled coordinated reset of neural subpopulations," Biol Cybern 89(2):81-88, Tass, 2003. See also "Long-term anti-kindling effects of desynchronizing brain stimulation: a theoretical study," Biol. Cybern 94(1):58-66, Tass, P. A., Majtanik M., and "Unlearning tinnitus-related cerebral synchrony with acoustic coordinated reset stimulation: theoretical concept and modelling," Biol. Cybern. 106(1):27-36, Tass and Popovych, 2012.

Using the systematic tonotopic organization of the peripheral and central auditory system in the auditory cortex in the temporal lobe, acoustic tones, typically having four different frequencies centered around the characteristic frequency of the patient's tinnitus percept, are determined and delivered in non-simultaneous sequences several hours per day for several weeks (Tass et al., 2012). The four tones are designed to activate different areas of the central auditory system in a coordinated manner.

Despite their relative sophistication, many known acoustic CR neuromodulation techniques do not provide or deliver acceptable therapeutic results to patients. What is needed are ways to improve the therapeutic effects provided by acoustic CR neuromodulation techniques.

SUMMARY

In one embodiment, there is provided a method of delivering a two-dimensional acoustic coordinated reset neuromodulation therapy to a patient's auditory cortex comprising evaluating a tinnitus pitch of the patient using a pitch matching method to determine a tinnitus center frequency; evaluating a tinnitus periodicity of the patient using a tinnitus periodicity estimation or determination method to determine a tinnitus periodicity; determining, for the patient, frequency and periodicity stimulation parameters corresponding to multiple therapeutic stimulation signals, where the frequency and periodicity parameters are calculated and generated on the basis of the patient's determined tinnitus pitch and tinnitus periodicity, the multiple therapeutic stimulation signals being configured to excite areas surrounding the center of tinnitus excitation in the patient's auditory cortex; and optionally delivering to the patient the multiple therapeutic stimulation signals thereby to treat the patient's tinnitus.

In other words, in one aspect there is provided a method of providing, particularly generating, stimulation signals for acoustic coordinated reset neuromodulation therapy. The method comprises evaluating a tinnitus pitch and a tinnitus timbre to determine a set of tinnitus parameters comprising at least a tinnitus pitch parameter and a tinnitus timbre parameter. The tinnitus pitch parameter (which may also be called tinnitus frequency parameter) describes a pitch (also called frequency or fundamental frequency or center frequency) of the tinnitus as experienced by the patient. The tinnitus timbre parameter (which may also be called tinnitus periodicity parameter) describes a timbre (also called periodicity) of the tinnitus as experienced by the patient.

Evaluation of the tinnitus pitch of the patient can be carried out by various pitch matching methods to determine a tinnitus pitch $f_T$ (also called center frequency or fundamental frequency) as experienced by the patient. For example, a tunable tone is delivered to the patient, while the patient adapts the pitch of the tunable tone until it matches the tinnitus pitch as experienced by the patient. Depending on the type of the tinnitus, the fundamental frequency of the tinnitus as experienced by the patient may be a center frequency of a noise or it may be a the fundamental tone, if the tinnitus is experienced as a tone-like tinnitus. Thus, in one aspect the fundamental frequency may be considered in the frequency domain as the greatest common divisor of all frequencies of a harmonic signal. Even if the fundamental frequency itself is not included in the spectrum of a tone, the pitch of that tone may still be perceived by a human as the pitch of a pure tone having said fundamental frequency, but having a different timbre. Thus, in this sense the frequencies of the overtones in a harmonic tone (or a harmonic component of a tone) correspond to the pitch of that tone, while the (relative) intensities of the overtones define its timbre.

Evaluation of the tinnitus periodicity (timbre) of the patient can be carried out by various tinnitus periodicity estimation or determination methods to determine a tinnitus periodicity (also called tinnitus timbre). In one preferred embodiment, this may comprise generating (and delivering to the patient) a (acoustic) timbre evaluation signal based on a combination of a first and a second evaluation signal with a tunable relative strength (or intensity) of the first and the second evaluation signal. In this composed signal, the first evaluation signal comprises a frequency corresponding to the determined tinnitus pitch parameter (i.e. the fundamental frequency of the tinnitus experienced by the patient), and the second evaluation signal comprises at least one frequency outside a predetermined fundamental frequency bandwidth around the frequency corresponding to the determined tinnitus pitch parameter. With tuning the relative strength/intensity of the two signal components, a resulting timbre of the timbre evaluation signal can be changed, specifically adapted or tuned, by the patient until the tuned timbre matches the patient's experience with the timbre of the tinnitus. Thus, the method preferably comprises receiving the patient's selection for a setting of the tunable relative strength, at which the generated acoustic timbre evaluation signal corresponds best with the tinnitus experienced by the patient. The tinnitus timbre parameter can then be determined based on the user selection. In particular, the tinnitus parameter may be determined as the ratio of the intensity or power of the second evaluation signal relative to the (overall) intensity or power of the tinnitus evaluation signal.

The timbre of the tinnitus evaluation signal can be efficiently tuned if the predetermined fundamental frequency bandwidth extends from about $0.5*f_T$, preferably from about $0.8*F_T$, more preferably from about $0.95*F_T$, even more preferably from about $0.99*F_T$, most preferably from about $0.995*F_T$ to about $2*f_T$, preferably to about $1.2*f_T$, more preferably to about $1.05*f_T$, even more preferably to about $1.01*f_T$, most preferably to about $1.005*f_T$. In a specifically preferred embodiment, the second evaluation signal comprises integer multiples of the fundamental frequency $f_T$. Preferably, the determined tinnitus timbre parameter defines a ratio of the power of frequency components in the tinnitus evaluation signal outside the predetermined fundamental frequency bandwidth relative to the overall power of the tinnitus evaluation signal.

Moreover, in one aspect of the present invention, the method comprises determining at least one set of stimulation parameters based on the set of tinnitus parameters, wherein the at least one set of stimulation parameters comprises at least a stimulation pitch parameter and a stimulation timbre parameter and generating at least one stimulation signal based on the determined at least one set of stimulation parameters.

Thus, in accordance with an aspect of the present invention, it has been proposed to apply a stimulation signal not only depending on a pitch of the tinnitus, but also depending on the experienced timbre of the tinnitus. While it has been known that adapting the frequency of a stimulation signal based on a frequency of the tinnitus is most efficient for a CR therapy, the present invention found that also adapting a timbre of the stimulation signal is highly efficient for the therapy. This is described by a two-dimensional matching of regions in the auditory cortex by means of the stimulation frequency as a first dimension and the stimulation timbre as a second dimension. Moreover, a stimulation signal adapted in its timbre based on the experienced tinnitus has proven to be particularly accepted by patients even when applied for many hours a day over a longer therapeutic period.

Preferably, the at least one set of stimulation parameters is determined based on the set of tinnitus parameters such that the stimulation pitch parameter and the stimulation timbre parameter are within a predetermined range relative to the tinnitus pitch parameter and the tinnitus timbre parameter. Most preferably, a stimulation timbre offset is applied, which defines an intentionally introduced shift of the stimulation timbre parameter in the at least one set of stimulation parameters as compared to the tinnitus timbre parameter. Thereby, a coordinated displacement of the stimulated region in the auditory cortex in the timbre dimension is achieved as compared to center of the region responsible for the tinnitus. With this two-dimensional adaption of the stimulation region in the auditory cortex, the intentional and coordinated shift of the stimulated region in a direction substantially perpendicular to a direction representative for the frequency enables to reduce an intentional shift in the frequency space (between the center of the tinnitus region and the stimulated region) without substantially increasing the total overlap of the tinnitus region and the stimulated region. Thus, with the coordinated stimulation which is selective in two-dimensions of the auditory cortex, multiple regions close to the region responsible for the tinnitus can be selectively and cooperatively stimulated without increasing an undesired overlap with the tinnitus region. In particular, even more than two regions next to (and around) the tinnitus region can be stimulated selectively in the auditory cortex. This is understood to be a reason for a high efficiency of the therapy and a high acceptance by patients.

Preferably, determining at least one set of stimulation parameters based on the set of tinnitus parameters comprises defining a two-dimensional parameter space spanned by a pitch parameter as a first dimension and a timbre parameter as a second dimension. The set of tinnitus parameters define a point (tinnitus point) in the two-dimensional space. Preferably, a maximum stimulation distance is provided as a predetermined value, e.g. considering the two-dimensional space spanned by the parameters as an Euclidean space. The at least one set of stimulation parameter may then be determined so that it defines a stimulation point in the two-dimensional space that is within the maximum stimulation distance from the tinnitus point.

Preferably, determining at least one set of stimulation parameters based on the set of tinnitus parameters further comprises providing a minimum stimulation distance as a predetermined value. Preferably, the at least one set of stimulation parameters is determined so that the stimulation point in the two-dimensional space is spaced from the tinnitus point by at least the minimum stimulation distance.

Preferably, determining at least one set of stimulation parameters comprises determining a plurality of sets of stimulation parameters based on the set of tinnitus parameters, each set of stimulation parameters comprising at least a stimulation pitch parameter and a stimulation timbre parameter; and wherein generating at least one stimulation signal comprises generating a plurality of stimulation signals, each stimulation signal being based on one of the determined sets of stimulation parameters.

Specifically, the plurality of (therapeutic) stimulation signals may comprise three (preferably four, more preferably six, even more preferably eight) separate (therapeutic) tones or signals, wherein each of the three (four, six, or eight) (therapeutic) tones or signals has a unique combination of frequency (i.e. pitch) and periodicity (i.e. timbre) associated therewith.

In a preferred embodiment, the method further comprises determining, for the patient, respective intensities for each of the plurality of (therapeutic) stimulation signals. This may specifically be done based on an individual hearing ability or hearing loss.

Preferably, determining a plurality of sets of stimulation parameters based on the set of tinnitus parameters comprises:
  defining a two-dimensional parameter space spanned by a pitch parameter as a first dimension and a timbre parameter as a second dimension;
  providing a minimum inter-signal distance as a predetermined value, e.g. when considering the parameter space as an Euclidean space; and
  determining the plurality of sets of stimulation parameters so that each set of stimulation parameters defines a stimulation point in the two-dimensional space, wherein for each pair of stimulation points (defined by the plurality of set of stimulation parameters) a distance between the stimulation points in the two-dimensional parameter space is at least the minimum inter-signal distance.

Specifically, the plurality of sets of stimulation parameters may comprise at least three sets of stimulation parameters, and the respective stimulation points in the two-dimensional parameter space form a (stimulation) polygon (e.g. a triangle in case of three sets of stimulation parameters) such that a tinnitus point defined in the two-dimensional parameter space by the set of tinnitus parameters is within said (stimulation) polygon (e.g. triangle). In this aspect, the plurality of stimulation points in the parameter space and thus the plurality of stimulation regions in the auditory cortex are not on the same line, but rather surround the tinnitus region in the auditory cortex, which is assumed to be responsible for the high efficiency of the therapy and the high acceptance by the patients.

In a preferred embodiment, the at least one stimulation signal is generated based on a combination (e.g. the sum) of a first and a second stimulation signal component with a relative strength of the first and the second stimulation signal component determined by the stimulation timbre parameter, wherein the first stimulation signal component comprises a frequency determined by the stimulation pitch parameter (i.e. the fundamental frequency of the tinnitus experienced by the patient), and the second stimulation signal component comprises at least one frequency outside a predetermined fundamental stimulation frequency bandwidth around the frequency determined by the stimulation pitch parameter, wherein a relative intensity of the second stimulation signal is determined by the stimulation timbre parameter.

Thus, the stimulation signal is composed of frequency components in a main band component (fundamental stimulation frequency bandwidth) and at least one side band component (outside the fundamental stimulation frequency bandwidth). In one example, the main band component may represent or include the fundamental frequency of a tone or a center frequency of a noise, while side band component may represent or include integer multiples (such as harmonics) of the fundamental frequency in case of a tone, or extended frequency band(s) in case of a noise. Preferably the side band component includes a higher frequency than the main band component. Specifically, the main band component and/or the side band components comprise substantially single distinct frequencies in case of a tone or extended frequency bands having a finite width in case of a noise. The center frequency of the main band component is preferably defined by the stimulation pitch parameter, while the relative strength of frequency components outside a range around the center frequency is preferably defined by the stimulation timbre parameter.

In one aspect multiple therapeutic stimulations signals, specifically as provided in one of the embodiments described herein is provided for use in creating a two-dimensional stimulation of the auditory cortex. Preferably they are used treating tinnitus.

In another embodiment, there is provided a system or device configured to deliver a two-dimensional acoustic coordinated reset neuromodulation therapy to a patient's auditory cortex comprising means for evaluating a tinnitus pitch of the patient using a pitch matching method to determine a tinnitus center frequency; means for evaluating a tinnitus periodicity of the patient using a tinnitus periodicity estimation or determination method to determine a tinnitus periodicity; means for determining, for the patient, frequency and periodicity stimulation parameters corresponding to multiple therapeutic stimulation signals, where the frequency and periodicity parameters are calculated and generated on the basis of the patient's determined tinnitus pitch and tinnitus periodicity, the multiple therapeutic stimulation signals being configured to excite areas surrounding the center of tinnitus excitation in the patient's auditory cortex, and means for delivering to the patient the multiple therapeutic stimulation signals thereby to treat the patient's tinnitus.

In other words, in one aspect a system or device is provided that is configured to provide/deliver stimulation signals for acoustic coordinated reset neuromodulation therapy, the system or device comprising:
  means for evaluating a tinnitus pitch and a tinnitus timbre to determine a set of tinnitus parameters comprising at least a tinnitus pitch parameter (which describes a pitch of the tinnitus as experienced by the patient) and a tinnitus timbre parameter (which describes a pitch of the tinnitus as experienced by the patient);
  means for determining at least one set of stimulation parameters based on the set of tinnitus parameters, wherein the at least one set of stimulation parameters comprises at least a stimulation pitch parameter and a stimulation timbre parameter;
  means for generating at least one stimulation signal based on the determined at least one set of stimulation parameters.

Preferably, the system or device is adapted to perform a method according to the present invention, specifically in accordance with one or more of the preferred embodiments described herein.

In yet another aspect, the present invention provide a computer program product, such as storage medium or a signal stream or preferably digital signals, comprising computer readable code, which when loaded and executed by a computer system, causes the computer system to perform operations according a method of the present invention, specifically in accordance with one or more of the preferred embodiments described herein.

Further embodiments are disclosed herein or will become apparent to those skilled in the art after having read and understood the specification and drawings hereof.

DETAILED DESCRIPTIONS OF SOME EMBODIMENTS

Described herein are various embodiments of systems, devices, components and methods relating to acoustic coordinated reset medical neuromodulation therapies delivered to patients via external and/or implanted systems, devices and components.

FIGS. 2a to 2d show different examples of timbre evaluation signals for determining a tinnitus timbre parameter.

FIG. 3 shows a schematic representation of stimulation signals for acoustic CR neuromodulation according to the prior art.

Figure 1:
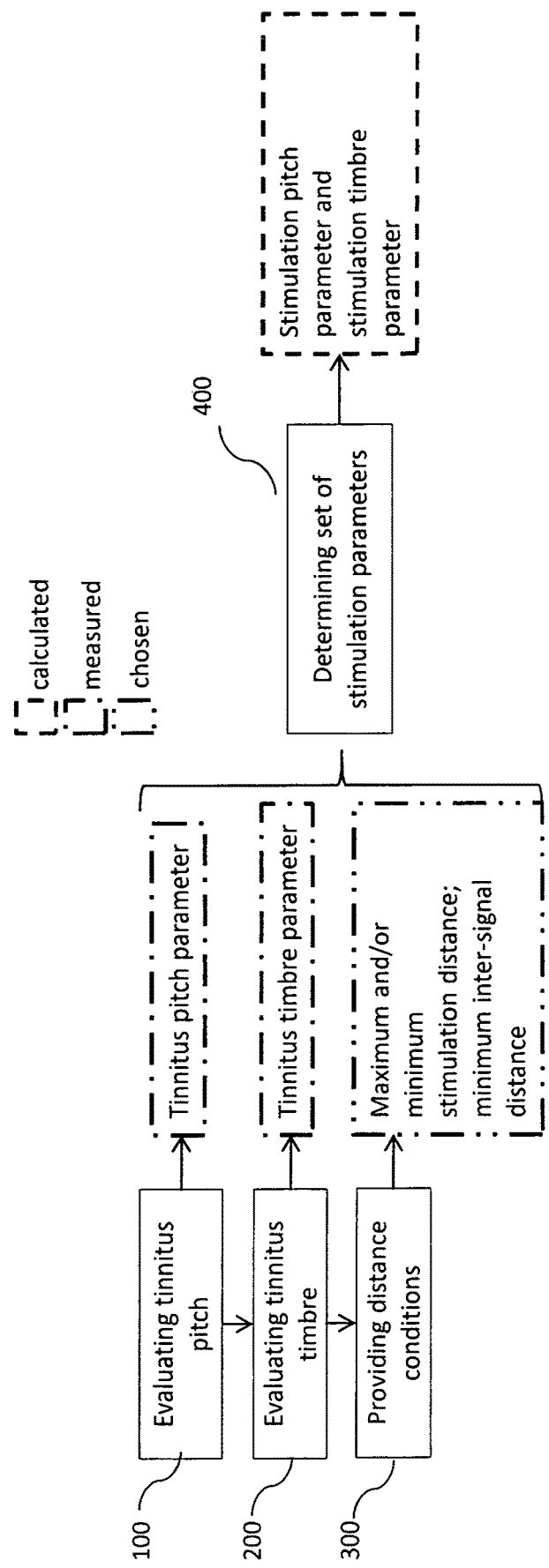
FIG. 1 shows a schematic representation of an exemplary method for acoustic CR neuromodulation according to the invention.

Tinnitus is the subjective perception of a sound in the absence of actual sound waves (also called acoustic waves). Since the perception is identical to the perception of an objectively-existing audio signal, tinnitus can nonetheless be described using audio signal characteristics. In particular, two sound parameters that may be useful in evaluating tinnitus are pitch and timbre.

An audio signal may be, but is not limited to, a pure tone signal, a harmonic signal, an inharmonic signal, a noise signal or a combination thereof.

A pure tone signal has a sinusoidal wave as waveform, i.e. the amplitude of the signal varies with time according to a sine function. A sine wave has a single, well-defined frequency, which is the number of full cycles per time unit. In the frequency domain representation (also called Fourier spectrum) the signal has only a peak or, more precisely, a Dirac delta function in correspondence of this frequency value. The pitch of a pure tone signal is its frequency, and also the timbre of a pure tone signal is characterized by its frequency.

Harmonic signals are given by the superposition of sinusoidal waves having different frequencies that are positive integer multiples of a common frequency, called fundamental frequency.

The Fourier spectrum of these signals is discrete with a plurality of peaks corresponding to the different frequencies. The pitch of a harmonic signal is the fundamental frequency. Inharmonic signals also have a discrete spectrum with a plurality of peaks, which however deviate from the harmonic integer-multiple positions. For analogy with the harmonic signals, a fundamental frequency is defined for inharmonic signals as the lowest frequency in the spectrum. Accordingly, also the pitch of an inharmonic signal can be defined as corresponding to the fundamental frequency, even if inharmonic signals do not actually produce a definite pitch perception in the human ear.

The frequencies that are above the fundamental frequency are called overtones and the set of overtones (also called harmonic content) is part of what defines the timbre. In particular, the timbre may be characterized by the spectral envelope derived from the Fourier spectrum. The spectral envelope is a curve in the frequency-amplitude plane that wraps around the Fourier spectrum, linking the peaks in a smooth manner so as to provide an overall profile of the amplitude of the signal as a function of the frequency. There are different ways of determining the spectral envelope, which include, but are not limited to, polynomial spline and cepstral windowing.

Although there are other factors contributing to the timbre of a sound as well, for the purposes of this application two signals having substantially the same spectral envelope are considered to have substantially the same timbre. For example, if two spectral envelopes are denoted by $S_1(f)$ and $S_2(f)$, wherein f is the frequency, the spectral envelopes may be considered to be substantially the same if $|S_1(f)-S_2(f)|/S_1(f)<A$ for all frequencies, with A being a constant. A may be e.g. 5%, or 3% or 1%.

A noise signal is a signal with a continuous (or noisy) Fourier spectrum instead of a discrete one. The continuous set of frequencies is usually delimited by an upper frequency $f_2$ and a lower frequency $f_1$, and the difference between the upper frequency and the lower frequency is called bandwidth BW. In particular, a narrow band noise signal has a relatively small BW in comparison to the audible range, e.g. BW=100 Hz or BW=20 Hz.

The spectral envelope and consequently the timbre can be defined for noise signals or combination of different kinds of signals analogously to the harmonic/inharmonic signals.

If the Fourier spectrum is substantially symmetric, the pitch of a noise signal may be defined as the geometric mean or the arithmetic mean of $f_1$ and $f_2$, which is called center frequency $f_c$.

If the Fourier spectrum is not symmetric, which could be the case for a signal given by a combination of different kinds of signals, e.g. harmonic plus noise, the pitch of a signal may also be defined in relation to the spectral envelope. The pitch may exemplarily be defined as that frequency $f_d$ such that:

$$\frac{\int_{f_d-\Delta f}^{f_d+\Delta f} S(f)df}{\int_{f_1}^{f_2} S(f)df} \geq B, \quad (1)$$

wherein $\Delta f$ may have a fixed value (e.g. $\Delta f/f=5\%$) or may be determined on a case-to-case basis. B may be a constant with value 25%, or 20%, or 15%.

In the following, in light of what explained above, the terms "pitch" and "frequency" will be used interchangeably. Further, the term "periodicity" will also be used to indicate the "timbre" for reasons that will become clear later.

A method of providing stimulation signals for acoustic coordinated reset neuromodulation therapy may comprise:
  evaluating a tinnitus pitch and a tinnitus timbre to determine a set of tinnitus parameters comprising at least a tinnitus pitch parameter and a tinnitus timbre parameter;
  determining at least one set of stimulation parameters based on the set of tinnitus parameters, wherein the at least one set of stimulation parameters comprises at least a stimulation pitch parameter and a stimulation timbre parameter;
  generating at least one stimulation signal based on the determined at least one set of stimulation parameters.

An exemplary implementation of this method is illustrated in FIG. 1.

According to this method, the tinnitus timbre is not just evaluated for a more precise characterization of the tinnitus but also so that a stimulation timbre can be determined according to it, as discussed later on.

Firstly, the tinnitus pitch is evaluated (step 100) to determine a tinnitus pitch parameter $f_T$ that describes the tinnitus pitch as experienced by the patient. The tinnitus pitch may be evaluated according to the pitch matching method described in the paper "Validation of a Mobile Device for Acoustic Coordinated Reset Neuromodulation Tinnitus Therapy" by Hauptmann et al., 2016. The tinnitus pitch evaluation may enable a quantitative description of the perceived tinnitus pitch via a numerical value for the tinnitus pitch parameter, which may be a frequency value in Hz.

In particular, the tinnitus pitch parameter may be determined as a characteristic frequency of the tinnitus experienced by patient. In light of what explained above, the characteristic frequency of the tinnitus may be the frequency of a pure tone signal, the fundamental frequency of a harmonic/inharmonic signal, the center frequency of a noise or the frequency $f_d$ according to equation (1) above.

Secondly, the tinnitus timbre is evaluated (step 200). The tinnitus timbre may be evaluated according to a timbre matching method in which a person affected by tinnitus is provided with evaluation means to identify a signal producing a sound that has substantially the same timbre as the tinnitus. In particular, the evaluation means may comprise generation means for generating at least a sample signal and output means for conveying the sample signal to a patient, e.g. loudspeakers or earphones, and input means that allow an operator and/or the patient to provide feedback to the generation means. The at least one sample signal may also be called "timbre evaluation signal" and may be an acoustic signal or be configured to be transformed into an acoustic signal (e.g. an electrical signal).

In one example, a single sample signal may be provided to the patient, who is enabled to modify the characteristics of the sample signal via the input means such as control knob or a combination of computer input devices (e.g. touchscreen, keyboard and mouse) and a graphical user interface. Specifically, the input means may allow the patient to change the timbre of the signal via a tunable parameter. Accordingly, the patient may manipulate the signal until the sound he hears resembles the tinnitus sound.

One possible way of providing a signal whose timbre can be adjusted via a quantitative tunable parameter, which can then be used to determine a stimulation timbre parameter, is the following. Two predetermined base signals may be used, wherein the base signals have the same pitch but different timbres. In particular, the pitch of the base signals may be the tinnitus pitch as previously evaluated.

A first base signal may have a Fourier spectrum comprising a frequency corresponding to the determined tinnitus pitch parameter, i.e. the characteristic frequency of the tinnitus as experienced by the patient. A second base signal may have a Fourier spectrum comprising at least one frequency outside a predetermined characteristic frequency bandwidth around the frequency corresponding to the determined tinnitus pitch parameter.

In some embodiments, the tunable parameter may define a ratio of the power of frequency components in the tinnitus evaluation signal outside the predetermined fundamental frequency bandwidth relative to the overall power of the tinnitus evaluation signal. The predetermined fundamental frequency bandwidth may extend from about 0.5 $f_T$, preferably from about 0.8 $f_T$, more preferably from about 0.95 $f_T$, even more preferably from about 0.99 $f_T$, most preferably from about 0.995 $f_T$ to about 2 $f_T$, preferably to about 1.2 $f_T$, more preferably to about 1.05 $f_T$, even more preferably to about 1.01 $f_T$, most preferably to about 1.005 $f_T$.

In one example, the first base signal has a spectral envelope dominated by low frequencies (i.e. the sound has a dark timbre) and the second base signal has a spectral envelope dominated by high frequencies (i.e. the sound has a bright timbre). Exemplarily, the first base signal may have a spectral envelope $SB_1$ and the second base signal may have a spectral envelope $SB_2$ such that $$\frac{\int_{f_1}^{f_g} SB_1(f)df}{\int_{f_1}^{f_2} SB_1(f)df} \geq C, \tag{2}$$

$$\frac{\int_{f_g}^{f_2} SB_2(f)df}{\int_{f_1}^{f_2} SB_2(f)df} \geq C, \tag{3}$$

wherein C may be 60%, or 75% or 90%, $f_1$ and $f_2$ are the smallest frequency and the largest frequency represented in the Fourier spectrum, respectively, and $f_g$ is a threshold frequency.

The threshold frequency may be for example the arithmetic mean of $f_1$ and $f_2$. In another example, the threshold frequency may be determined with respect to the tinnitus pitch. For instance, the threshold frequency may be $f_g=1.5$ $f_T$, or $f_g=2$ $f_T$, or $f_g=2.5$ $f_T$.

In another example, the first base signal may be a pure tone signal and the second base signal may be an acoustic signal with a spectral envelope dominated by high frequencies, similarly to the first example. In particular, the second base signal may be a harmonic signal in which the fundamental frequency and, optionally, the first overtone, or the first and second overtones, are missing. An example of such base signals is shown in FIG. 2a. FIG. 2a shows on the left a schematic representation of a Fourier spectrum of a first base signal, which is a pure tone signal, and on the right a schematic representation of a Fourier spectrum of a second base signal, which is a harmonic signal in which the fundamental frequency is missing.

The sample signal can be given by a weighed combination or superposition of the first base signal and the second base signal, wherein the weight is the tunable parameter that changes the timbre. In other words, the relative strength of the first and second base signals is tunable. Schematically, if the first base signal is $B_1(t)$ and the second base signal is $B_2(t)$, the sample signal $S(t)=w_1 \cdot B_1(t)+(1-w_1) \cdot B_2(t)$, with $w_1$ being the weight, $w_1 \in [0, 1]$. It should be understood that the above formula is not a rigorous mathematical equation but rather a symbolic representation of the combination of the two signals. The combination of the base signals may entail the introduction of a phase offset between the base signals. Exemplarily, if the two base signals are harmonic signals $B_1(t)=a_0+\Sigma_{n=1}^{N}a_n \sin(2\pi n f_T t + \varphi_1)$ and $B_2(t)=b_0+\Sigma_{n=1}^{N}b_n \sin(2\pi n f_T t + \varphi_2)$, the sample signal may be given by the equation $$S(t) = w_1 B_1(t) + (1-w_1)B_2\left(t - \frac{d}{f_2}\right), \tag{4}$$

wherein $a_0$, $a_n$, $b_0$, $b_n$ are amplitude parameters, $\phi_1$ and $\phi_2$ are the phases and d is a phase shift parameter.

Another possible way of generating a timbre evaluation signal with a tunable parameter that changes the timbre is the following. The signal S(t) may be defined as:

$$S(t) = \begin{cases} \sin\left(2\pi \cdot \frac{f}{PD}t\right) & \text{for } t \in \left]0 + \frac{n}{f}, \frac{n \cdot PD}{f}\right] \\ 0 & \text{for } t \in \left]\frac{n \cdot PD}{f}, \frac{n}{f}\right] \end{cases} \tag{5}$$

where $n \in \mathbb{N}$, t is the time in seconds and f is the pitch of the signal in Hz, which could be set to $f_T$.

This signal is a "compressed" sinewave, which maintains the same frequency f or period T of a standard sinusoid signal, but is a harmonic signal including overtones. The range of time in which the signal is different from zero is given by T·PD. Accordingly, the parameter PD could be seen as introducing a "second period" for the sinusoidal part and therefore it is also called periodicity. Since the variation of this parameter changes the harmonic content of the spectrum, and, thus, the timbre, the terms "timbre" and "periodicity" are used interchangeably.

Accordingly, the signal is controlled by the parameter PD, whose values can in principle range from values greater than 0 up to 1. The actual values of the parameter PD depend on the frequency f and the sampling rate of the signal. The smallest possible value of PD/f has to contain 5 samples of the discrete signal to allow building a full sinus wave. E.g. for typical frequencies of f up to 10000 Hz, sampling rates of 528000 Hz would be needed to realize values of $PD \in ]0.1, 1]$.

FIG. 2b shows two signals with a period of 0.002 sec, resulting in a fundamental frequency of 500 Hz. On the left side the parameter PD equals 1.0 and on the right side the PD equals 0.2.

A third possibility for generating a sample signal with a control parameter that influences the timbre is the following. The sample signal may be generated using amplitude modulation with a specific modulation rate on a carrier signal. The carrier signal can be a narrow band noise signal with a specific center frequency, exemplarily ranging from 0 to 16,000 Hz, and with a specific bandwidth of the narrow band, defined in Hz (e.g. 20 Hz or 100 Hz) or as a percentage of the center frequency, ranging from 0% to 100% (e.g. 1.5%).

The amplitude modulation as a function of time may be defined as m(AMR,t)=0.5*(1+sin(2π*AMR*t)), wherein the parameter AMR is the amplitude modulation rate. In some examples, the AMR could range from 0 to 16,000 Hz, more specifically from 0 to 5000 Hz, further specifically from 2 to 300 Hz, yet further specifically from 30 to 100 Hz.

A tuning parameter PD that varies from 0 to 1 may be introduced to obtain different regimes in the variation of the amplitude modulation. For example, the sample signal S(t) may be defined as:

$$S(t) = \begin{cases} (5*PD)*m(16 \text{ Hz}, t)*CS(t) + \\ (1-5*PD)*CS(t) & \text{for } PD \in [0, 0.2] \\ m(PD*300 \text{ Hz} - 44 \text{ Hz}, t)*CS(t) & \text{for } PD \in ]0.2, 1] \end{cases} \quad (6)$$

wherein CS is the carrier signal.

For PD in the range from 0 to 0.2, an amplitude modulated signal with an AMR of 16 Hz will be mixed with the pure carrier signal in a linear way so that for 0% the pure carrier signal will be used and for 20% the pure amplitude modulated signal will be used.

For PD in the range from 0.2 to 100, the amplitude modulation varies linearly between 16 Hz (20%) and 256 Hz (100%).

The interval limits of 16 Hz and 256 Hz and also the threshold of 0.2 are just one exemplary implementation.

Figure 2C:
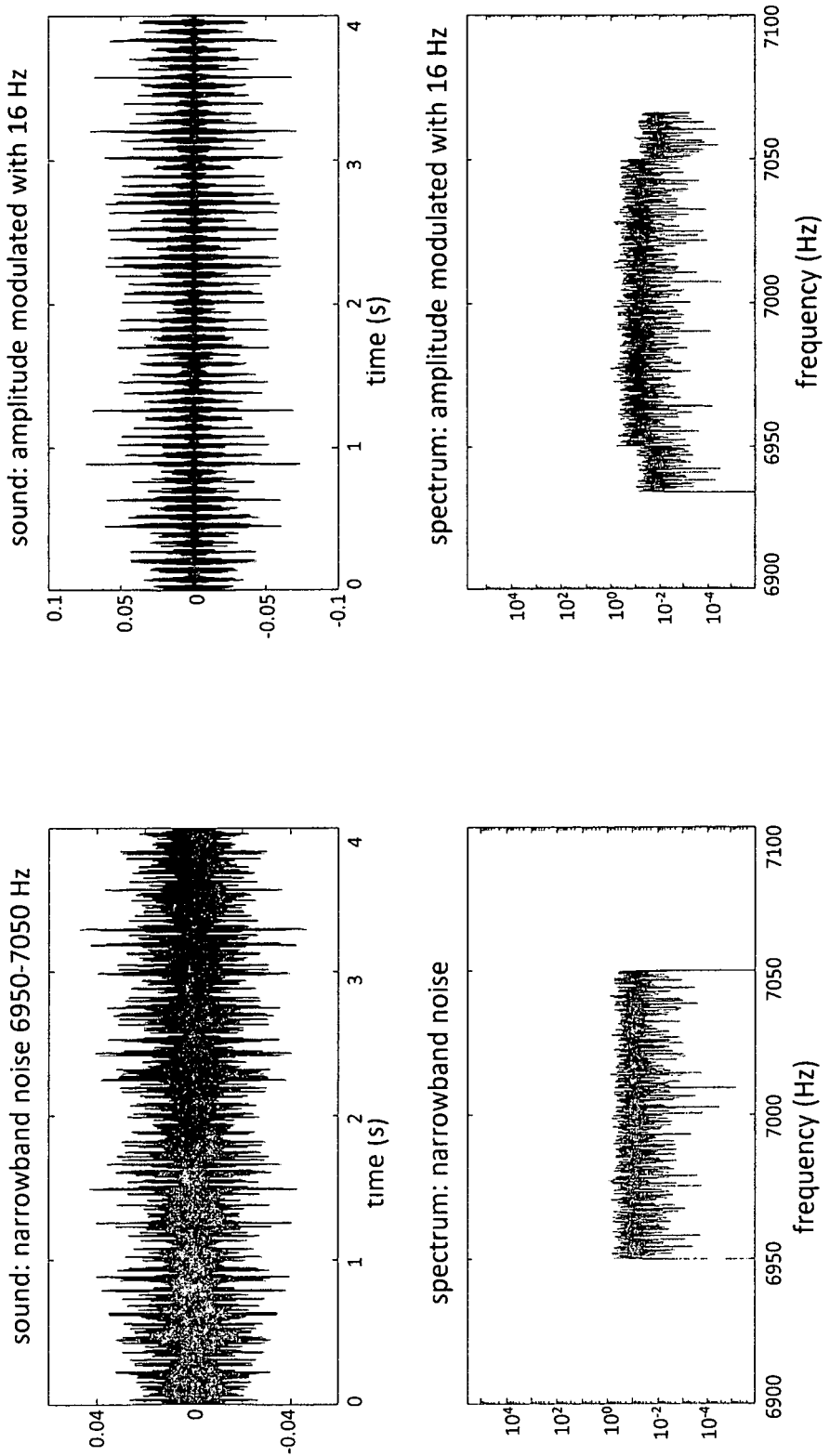
Figure 2D:
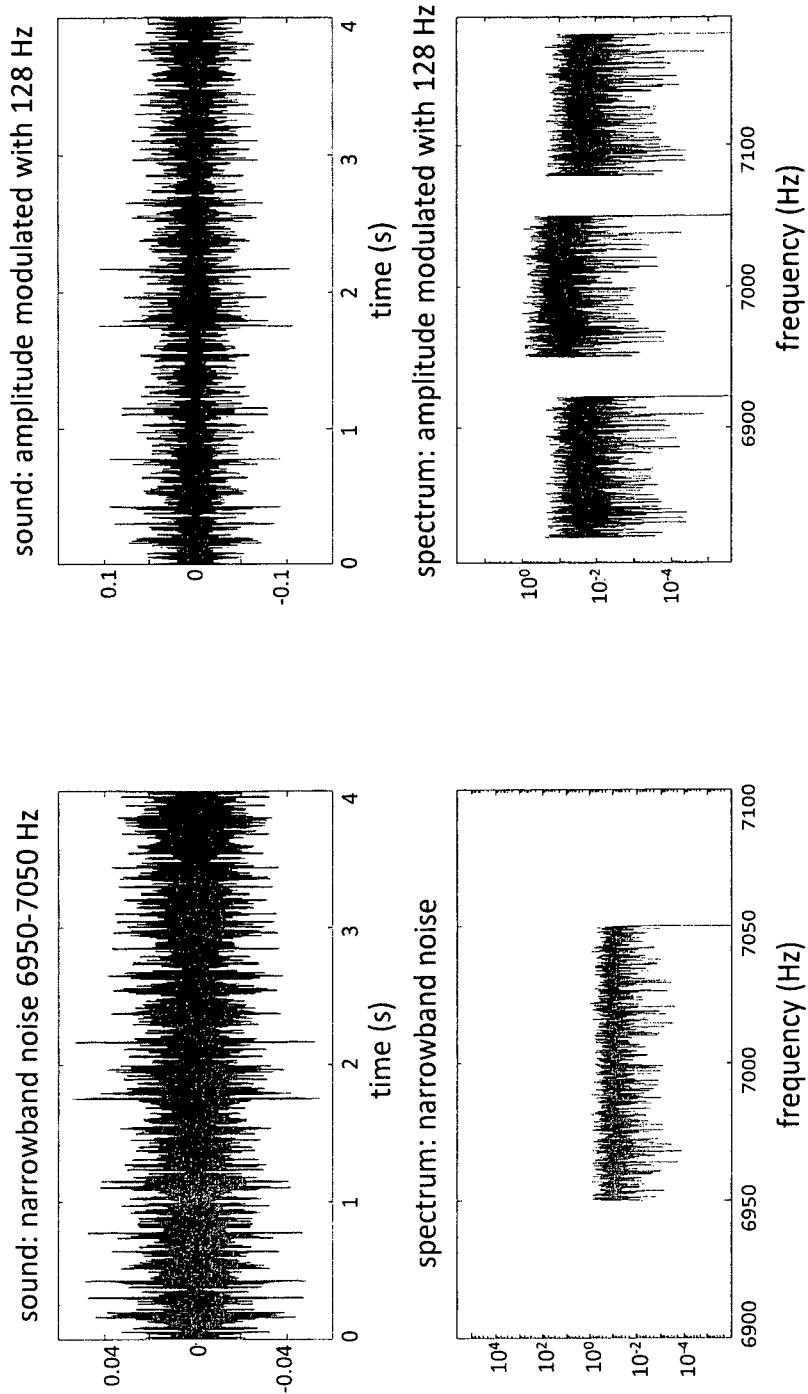

As shown in FIGS. 2c and 2d, the Fourier spectrum and corresponding spectral envelope for two different values of PD, 0.2 and 0.57, are different, and consequently the timbre of the signals with different PD values are different.

In summary, the step 200 of evaluation of the tinnitus timbre involves the generation of a timbre evaluation signal whose timbre is adjustable via of a quantitative tunable parameter (e.g. $w_1$ or PD) that defines the timbre of the sample signal. As mentioned, the patient is provided with input means so that a patient's selection for a setting of the tunable parameter can be received. Specifically, the patient is supposed to adjust the tunable parameter until the generated timbre evaluation signal corresponds best with the tinnitus as experienced. Accordingly, the tinnitus timbre parameter $p_T$ is determined based on the user's selection.

This approach to evaluating the tinnitus timbre is unlike known approaches, in which the patient is led to selecting a tone that resembles the tinnitus sound e.g. by iterative comparison of a set of tones. In particular, the herein described characterization of the timbre allows the possibility of deriving a timbre-related well-defined control parameter of the stimulation signals used in CR therapy, as will be explained in the following.

The term "stimulation signal" may be used to denote both an electrical signal that is converted into an acoustic wave perceivable by a patient and an acoustic wave itself, which could be generated also in a different way. In the following, the terms "tone" and "stimulation signal" may be used interchangeably.

Conventional CR therapy methods employ pure tone signals to treat tinnitus, wherein the pure tone stimulation signals have different pitches that are determined in relation to the tinnitus pitch.

FIG. 3 shows a schematic representation of stimulation signals according to a conventional method. The shaded area represents the primary auditory cortex 10 of a patient, which is tonotopically organized, meaning that neighboring cells in the cortex respond to neighboring frequencies. The area activated by the tinnitus 20 is a part of the cortex and, for example, four stimulation signals activate areas 22, 24, 26 and 28 close to the tinnitus 20. In particular, the stimulation signals have frequencies $f_1$, $f_2$, $f_3$ and $f_4$, respectively, with $f_1<f_2<f_T<f_3<f_4$. The only varying parameter in the stimulations signals is the frequency, so that the parameter space is one-dimensional. Due to the tonotopicity of the cortex, the one-dimensionality of the stimulation signals in the parameter space is reflected into the physical location of the activated areas 22, 24, 26 and 28, which are arranged substantially in a line.

Here we describe and outline a novel two-dimensional approach to acoustic CR neuromodulation for treating Tinnitus, Parkinson's disease, and potentially other diseases or maladies, which employs frequency and periodicity as control parameters.

The scientific literature provides hints that stimulation tone frequencies and periodicities may be represented in orthogonal maps of the human auditory cortex. See, for example, "Frequency and periodicity are represented in orthogonal maps in the human auditory cortex: evidence from magnetoencephalography," Langner et al., December, 1997, J. Comp. Physiol. A 181, 665-676; and "A map of periodicity orthogonal to frequency representation in the cat auditory cortex," Langner et al., November, 2009, Frontiers Integr. Neurosci., Volume 3, Article 27, 1-11. As disclosed herein, certain aspects of the concepts disclosed in the foregoing Langer et al. publications are adapted and modified to effect suitable 2-D stimulation of the auditory cortex.

In some approaches, the frequencies of CR neuromodulation stimulation tones are adjusted with respect to the tinnitus pitch and changed to optimally arrange the tones in a two-dimensional arrangement around the site in the auditory cortex where the tinnitus pitch is generated. The auditory cortex is not a one-dimensional structure. Instead, the auditory cortex is a three-dimensional structure, which may be modelled as a two-dimensional or three-dimensional structure.

As a pre-requisite for this type of novel 2-D stimulation, both the frequency and the periodicity of the tinnitus are evaluated in order to determine a set of tinnitus parameters, as explained above, and not only the tinnitus pitch or frequency, as has been done up to now. This information regarding tinnitus frequency and periodicity is then employed in a two-dimensional tinnitus pitch matching algorithm to calculate and then apply suitable therapeutic stimulation tones or signals, where both frequency and periodicity are taken into account.

The 2-D stimulation tone configuration can be achieved by changing the periodicity of the stimulation tones together with the frequency, which causes the stimulation signals to excite areas surrounding the center of tinnitus excitation in the patient's auditory cortex in a two-dimensional arrangement. More specifically, the stimulation signals are generated on the basis of two different parameters, pitch and timbre, so that each signal can be represented by a point in the two-dimensional parameter space where the pitch is one dimension and the timbre is the other dimension. Consequently, since the pitch and the timbre may be represented in orthogonal maps of the auditory cortex, the two-dimensional parameter space is reflected in an actual two-dimensional activation of the cortex.

After determining the set of tinnitus parameters as described above, at least one set of stimulation parameters is determined based on the set of tinnitus parameters, wherein the at least one set of stimulation parameters comprises at least a stimulation pitch parameter and a stimulation timbre parameter. This corresponds to exemplary step 400 of FIG. 1.

As explained, using two control parameters, namely the pitch and the timbre, enables one or more stimulation signals to excite areas in the cortex that are located in a two-dimensional space around the center of tinnitus excitation. Conversely, when only the frequency is used as control parameter for the stimulation signals, as it is conventionally done, only areas along a one-dimensional space can be excited. Therefore, taking the periodicity into account broadens the range that can be treated by the stimulation signals, allowing to reach areas that are precluded to conventional methods. Accordingly, even a single stimulation signal can achieve a 2-D stimulation, in the sense that it excites an area located in a two-dimensional space around the center of tinnitus excitation.

In some embodiments, determining at least one set of stimulation parameters comprises determining a plurality of sets of stimulation parameters based on the set of tinnitus parameters, each set of stimulation parameters comprising at least a stimulation pitch parameter and a stimulation timbre parameter. Generally, the stimulation pitch parameters and stimulation timbre parameters of a plurality of stimulation signals can be denoted with $f_i$ and $p_i$, respectively, with i=1, . . . , n. As mentioned, at least one stimulation signal with $f_1$ and $p_1$ is required. When a plurality of signals is employed, at least one of the following conditions is satisfied $\forall i \neq j$: $f_i \neq f_j$ or $p_i \neq p_j$.

The stimulation parameters of each signal may be determined as a function of the tinnitus parameters, i.e. $f_i = g_i(f_T)$ and $p_i = h_i(p_T)$. The specific form of the functions $g_i$ and $h_i$ should be determined so that the subsequently generated signals activate areas in proximity of the center of tinnitus excitation and, at the same time, they can be perceived by the patient as two different tones. Consequently, there are two requirements for $g_i$ and $h_i$.

First, the functions should be chosen so that the activated areas lie close to the tinnitus center, in order to improve the efficacy of the treatment. Secondly, the functions should be chosen so that the stimulation parameters are sufficiently different from each other and from the tinnitus parameters to give rise to differently-perceived tones. Two tones are perceived as different, if the auditory activity caused by the two tones is processed in two different neuronal areas. Accordingly, the brain organization and the cochlear organization define the constraints for this second requirement.

Figure 4:
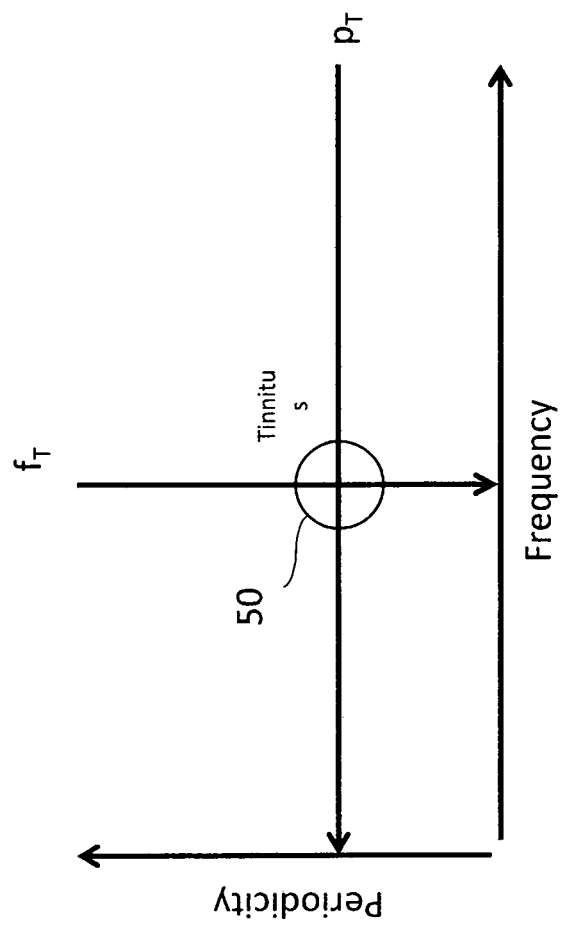
FIG. 4 shows a tinnitus point in a two-dimensional parameter space.

The first condition must hold for each stimulation signal independently from the other. Considering the two-dimensional parameter space spanned by a pitch parameter as a first dimension and by a timbre parameter as a second dimension, the set of tinnitus parameters defines a tinnitus point 50 in this space, as shown in FIG. 4. In order to implement the first condition, a maximum stimulation distance may be provided based on therapeutic considerations, such as the efficacy of the treatment. Accordingly, the maximum stimulation distance may be a predetermined value derived e.g. from tests on patients.

The at least one set of stimulation parameters is determined so that it defines a stimulation point in the two-dimensional space that is within the maximum stimulation distance. For example, if $E_1$ is a normalized maximum stimulation distance, then $f_i$ and $p_i$ may be determined according to the following equation:

$$\frac{\sqrt{|f_i - f_T|^2 + |p_i - p_T|^2}}{f_T^2 + p_T^2} \leq E_1, \qquad (7)$$

wherein $E_1$ is a constant value that may be equal to e.g. 0.2 or 0.1. At least one of the stimulation parameters must be different from the corresponding tinnitus parameter, i.e. either $f_i \neq f_T$ or $p_i \neq p_T$.

The second condition may be implemented by providing a minimum stimulation distance and/or a minimum inter-signal distance. The values for these distances may be predetermined e.g. on the basis of the patient physiology. The minimum stimulation distance and the minimum inter-signal distance may coincide or not.

When a minimum stimulation distance is provided, the at least one set of stimulation parameters is determined so that the stimulation point in the two-dimensional space is spaced from the tinnitus point by at least the minimum stimulation distance. For example, if $E_2$ is a predetermined value for a normalized minimum stimulation distance, the stimulation parameters may be determined according to the following equation:

$$\frac{\sqrt{|f_i - f_T|^2 + |p_i - p_T|^2}}{f_T^2 + p_T^2} \geq E_2, \qquad (8)$$

wherein $E_2$ may be equal to e.g. 0.4 or 0.2.

When providing a minimum inter-signal distance, the plurality of sets of stimulation parameters is determined so that each set of stimulation parameters defines a stimulation point in the two-dimensional space, wherein for each pair of stimulation points a distance between the stimulation points in the two-dimensional parameter space is at least the minimum inter-signal distance. For example, if $E_3$ is a predetermined value for a normalized minimum inter-signal distance, the stimulation parameters may be determined according to the following equations:

$$\frac{\sqrt{|f_i - f_j|^2 + |p_i - p_j|^2}}{f_T^2 + p_T^2} \geq E_3 \forall i \neq j,$$

wherein $E_3$ may be equal to e.g. 0.4 or 0.2.

It is worth noting that in a two-dimensional space in the cortex around the center of tinnitus excitation the areas activated by the stimulation signals may advantageously be closer to the center of tinnitus excitation, as a whole, in comparison with the known methods. It can be seen from FIG. 3 that areas 22 and 28 are farther apart from the tinnitus area 20, in order for the signals to be still perceived as different tones. With an additional dimension, the excited areas can be located e.g. in a circular path around the tinnitus area, i.e. at the same distance therefrom, while at the same time being sufficiently distant from the each other.

In one example, the functions $g_i$ and $h_i$ may be parameterized as follows: $g_i(f_T)=m_i*f_T$ and $h_i(p_T)=n_i*p_T$, wherein $m_i$ and $n_i$ are constant factors. In other examples, an offset may be included in these linear relations, or the functions may be non-linear in the tinnitus parameters.

In summary, the functions $g_i(f_T)$ and $h_i(p_T)$ may be defined to satisfy the conditions listed above. In the above example, the frequency and periodicity factors $m_i$ and $n_i$ may be chosen to comply with the constraints. Once the form of the functions $g_i(f_T)$ and $h_i(p_T)$ is defined as a consequence of the distance conditions (step 300 in FIG. 1), the stimulation parameters can be calculated (step 400 in FIG. 1).

In one embodiment, the plurality of sets of stimulation parameters comprises at least three sets of stimulation parameters, and the respective stimulation points in the two-dimensional parameter space from a triangle such that the tinnitus point defined in the two-dimensional parameter space by the set of tinnitus parameters is within said triangle. In one example, the triangle may be substantially equilateral and the tinnitus point may be at the center of it.

In another embodiment, the plurality of sets of stimulation parameters comprises at least three sets of stimulation parameters. The four sets of stimulation parameters, which take into account the patient's tinnitus pitch or frequency and the patient's tinnitus periodicity, may be calculated as follows:

Set 1: $f_1=0.8*f_T$, $p_1=0.8*p_T$

Set 2: $f_2=0.8*f_T$, $p_2=1.2*p_T$

Set 3: $f_3=1.2*f_T$, $f_3=0.8*p_T$

Figure 5:
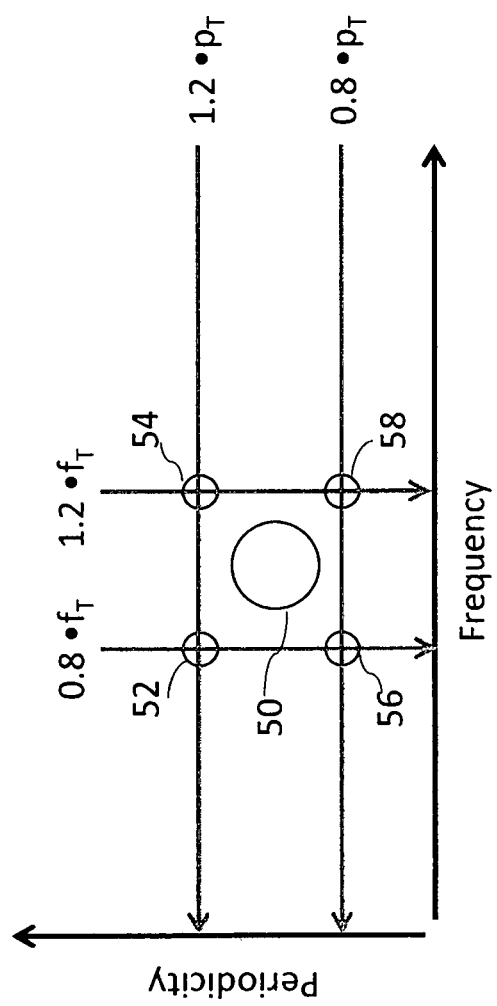
FIG. 5 shows stimulation points in a two-dimensional parameter space.

Set 4: $f_4=1.2*f_T$, $f_4=1.2*p_T$, where $f_T$=frequency of tinnitus, and $p_T$=periodicity of the tinnitus. From these values and parameters a stimulation configuration or regime such as that shown above in FIG. 6 may be derived. In particular, FIG. 5 shows the four stimulation points 52, 54, 56 and 58 corresponding to the above four sets of stimulation parameters in the two-dimensional parameter space.

Note that other numbers of therapeutic stimulation tones or signals are also contemplated, such as one, three, five, six, seven, eight, and so on.

After having determined the stimulation parameters for a stimulation signal, the stimulation signal is generated based thereon. If a plurality of sets of stimulation parameters ($f_i$, $p_i$) has been determined, a plurality of stimulation signals is accordingly generated. In particular, in order to generate a signal with a timbre parameter $p_i$, given the frequency $f_i$, the methods described above with reference to generating timbre evaluation signals may be similarly employed.

Figure 6:
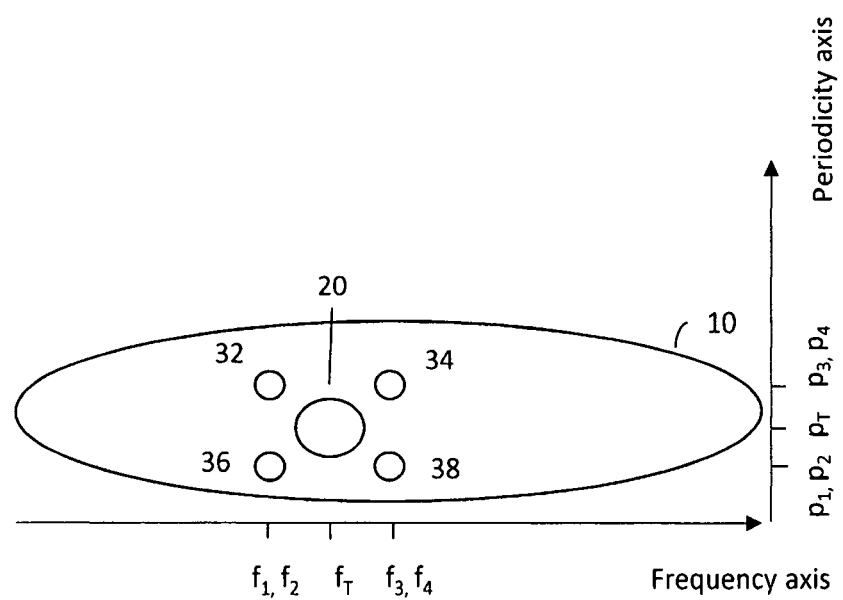
FIG. 6 shows an exemplary schematic representation of stimulation signals for acoustic CR neuromodulation according to the invention.

The stimulation signals obtained according to the method explained above can then be used for stimulating the cortex of a patient. In one embodiment, four test tones, tones or therapeutic frequencies are designed to activate different areas of the central auditory system in a coordinated manner. As described above, note that fewer or more such tones may be employed, in upper and lower frequency pairs or otherwise (e.g. singly or in combinations of odd and/or even numbers). FIG. 6 shows an example in which different areas of a cortex 10 are shown. In particular, the area activated by the tinnitus 20 is surrounded by the four areas 32, 34, 36 and 38 activated by the four stimulation signals. In particular, the four stimulation signals have sets of stimulation parameters ($f_1$, $p_1$), ($f_2$, $p_2$), ($f_3$, $p_3$) and ($f_4$, $p_4$), determined as described for FIG. 5 above.

In one example, the generated stimulation signals are electrical signals whose amplitude represents a voltage. These electrical signals can be converted into sound by means of a transducer, e.g. a loudspeaker.

A single stimulation signal may be delivered to a patient at a given rate. If multiple stimulation signals are used, the tones are delivered sequentially, i.e. there is no overlap of the tones.

Tones may be delivered continuously or there may be intervals of non-delivery, i.e. pauses, in between. A segment of the delivery between two pauses may be called a sequence.

In one example, the tones may be delivered in a random manner, meaning that there is no predetermined order in the succession of the tones in a sequence. The randomness may be boundless, in that the occurrence of each tone in the sequence may be equally probable at each moment. In other cases, some constraints may be given that at least partially govern the delivery of the tones. For example, the occurrence of each may be determined according to probability distributions that may be computed on the basis of therapeutic considerations. Additionally or alternatively, rules may be implemented, according to which e.g. the same tone cannot be repeated twice consecutively and/or all tones must appear at least once in the sequence and/or a certain tone cannot follow another tone. In some examples, each tone occurs once and only once in a sequence.

The delivery of tones in different sequences can obey the same constraints or not. The durations of the sequences can be the same for all sequences or not and, similarly, the lengths of the pauses can be the same for all pauses or not.

The rate of the delivery of the sequences may be related to the incidence of the tinnitus, so that e.g. all tones are played at least once in a certain period of time computed on the basis of such incidence.

In some embodiments, the selection of such tones or, more specifically, of their therapeutic frequencies is optimized by adapting the spread of the tones or therapeutic frequencies with respect to the intensity of each of the individual tones, as well as optionally with respect to the hearing thresholds of the patient being treated. In one embodiment, a built-in microphone can be used to adjust the intensity of the stimulation tones with respect to ambient or environmental noise, and the newly adjusted tones can then be corrected for above-threshold intensities.

Until now CR therapy tones have been fixed and selected with respect to the tinnitus pitch without considering that increased stimulation tone intensities can be compensated for by choosing wider spreads. Currently used tones are only optimal for a particular intensity band. If the stimulation tone intensity needs to be adjusted outside the standard or conventional range (e.g., because of individual hearing thresholds), stimulation tones can become suboptimal and therapeutic outcome for patients can be reduced.

Based on a current stimulation intensity (dB above threshold), stimulation frequencies can be changed instantaneously or nearly instantaneously (where some delay or inertia is applied to prevent over-rapid changes in the intensity of the stimulation that is delivered). If the patient changes the intensity of the stimulation signal, or the intensity is changed automatically by the device delivering the stimulation, the frequencies of the stimulation tones are changed and/or adapted accordingly (i.e., stimulation tone frequencies are changed if the stimulation intensity is modified). No fixed stimulation signal is programmed. Instead, a stimulation algorithm utilizing dB hearing loss (HL) information from a patient assessment and current master volume settings are used to instantaneously define optimal stimulation frequencies. A thresholdogram obtained during the patient assessment is stored and used by an algorithm such that for any set of frequencies a balanced set of stimulation tones can be defined. For high intensity stimulation applications, a wide spread of stimulation tones may be required.

Some type of inertia or delay may be employed to avoid over-rapid adjustments in stimulation intensity delivered to the patient. Using such techniques, an iPod configured to carry out the methods described herein can be programmed and configured to automatically adjust the intensity of the delivered stimulation, and no intervention by the patient is required. Together with automatic adaptation of the stimulation frequencies, stimulation is optimized and stimulation outcomes are improved. In one embodiment, a stimulation adaptation algorithm is configured to enable programming automated stimulation frequency adjustments based on an above-threshold dB level of stimulation.

A thresholdogram may be obtained during patient assessment and stored for use by the algorithm such that for any frequencies a balanced set of stimulation tones can be defined. Using such techniques, the algorithm/software can determine the appropriate intensity (dB HL for the individual patient) corresponding to each of the stimulation tones and for the present environmental or ambient noise level. For each stimulation tone, the optimal frequency in relation to the pitch frequency (tinnitus frequency) is calculated. The frequency of the stimulation tone is then re-adjusted and the local amplitude requirements are checked again. Using such an iterative process, stimulation frequency and amplitude levels are optimized. For higher-intensity stimulation applications a wide spread of stimulation tones may be required.

In addition, recorded patient feedback may be recorded and then employed to adjust or change therapeutic stimulation signal center frequencies, therapeutic stimulation signal intensities, amounts of overlap between therapeutic stimulation signals, therapeutic stimulation signal ABF and/or ERB widths, and/or therapeutic stimulation signal periodicities. Equivalent rectangular bandwidths (or ERBs) are understood to be only a particular type of auditory filter bandwidth (or AFB).

The various embodiments disclosed and described herein may also be adapted and configured to treat diseases other than tinnitus, such as Parkinson's disease.

Some of the calculations, methods, algorithms, equations and/or formulas used to calculate or determine specific tones or frequencies, frequency and periodicity stimulation parameters, auditory filter bandwidths (including equivalent rectangular bandwidths or EBRs), the amount of overlap between adjoining tones or frequencies, and/or the intensity of stimulation that is to be delivered to a patient are derived in part from published sources (e.g., Hopkins and Moore, 2011).

It is to be understood that these calculations, methods, algorithms, equations and/or formulas are merely illustrative, and that other suitable calculations, methods, algorithms, equations and/or formulas may be employed to attain the same, or substantially the same, results.

In Hopkins and Moore, 2011, the perception of sound under different situations, and in particular for different sound intensity levels, is studied. Therapeutic stimulation is not a topic of this article. One equation from Hopkins and Moore, 2011, is employed in the following pages to design an effective therapeutic stimulation regime for reducing the effects of tinnitus. This equation is used to space therapy tones apart from one another such that distinct sub-populations of the neuronal network are stimulated by each of the four stimulation tones, which is intended to provide an optimal desynchronizing effect of the stimulation and accordingly provide maximum therapeutic benefit to the patient.

One of the key issues explored in Hopkins and Moore, 2011 is the effect of human hearing loss and age on frequency selectivity. One portion of the study presented by Hopkins and Moore, 2011, provides an intuitive mathematical formula that enables rapid estimation of auditory filter bandwidths to permit further investigation of the correlation between human hearing loss and age on the one hand, and frequency selectivity on the other hand. In one embodiment, we apply the formula of Hopkins and Moore, 2011, to permit fine tuning of a pre-existing acoustic stimulus therapy for tonal subjective tinnitus. That is, we do not apply the formulae disclosed by Hopkins and Moore, 2011, to research frequency selectivity in humans. Instead, we calculate one AFB and/or ERB for below the tinnitus frequency and one AFB and/or ERB for above the tinnitus frequency. We use these approximations for an overlap calculation of tones or frequencies 1 through 4. By doing so we avoid the need to perform numerous iterations that would likely not improve precision or therapeutic performance by very much (but which according to some embodiments may be carried out).

Moreover, in some embodiments the order in which AFB and/or ERBs and stimulation intensities are calculated may be reversed, since in the general case the intensity of the stimulation tones is obtained before the AFB and/or ERBs can be calculated. Consequently, the expected intensity of the stimulation tones can be approximated initially and iteratively as a final intensity of stimulation is initially unknown.

Upon having read and understood the specification and claims of the present patent application, those skilled in the art will immediately understand and appreciate that other mathematical equations and formulas, or modified mathematical equations and formulas, may be employed advantageously to attain the same or substantially the same results without departing from the scope and spirit of the present invention.

The systems, devices, components, and methods disclosed in various publications may also be modified advantageously in accordance with the teachings set forth herein. Such publications include, but are not limited to, the following publications, copies of which are attached hereto in Appendix B: (a) "The effects of age and cochlear hearing loss on temporal fine structure sensitivity, frequency selectivity, and speech reception in noise," Hopkins and Moore, J. Acoust. Soc. Am. 130 (1), 334-349 (2011); (b) "The effect of hearing loss on the resolution of partials and fundamental frequency discrimination," Moore and Glasberg, J. Acoust. Soc. Am. 130 (5), 2891-2901 (2011); (c) "Acoustic Coordinated Reset Neuromodulation in a Real Life Patient Population with Chronic Tonal Tinnitus," Hauptmann et al., BioMed Research International Article ID 569052, Hindawi Publishing Corporation (2015); (d) "Acoustic CR neuromodulation therapy for subjective tonal tinnitus: a review of clinical outcomes in an independent audiology practice setting," Williams et al., Front. Neurol. (2015); (e) "Validation of a Mobile Device for Acoustic Coordinated Reset Neuromodulation Tinnitus Therapy," Hauptmann et al., J. Am. Acad. Audiol. 00:1-12 (2016), and (f) "optimal number of stimulation contacts for coordinated reset neuromodulation," Lysyansky et al., Frontiers in Neuroengineering, Vol. 6, pp 1-15 (2013).

According to some embodiments, there is provided a method of delivering a two-dimensional acoustic coordinated reset neuromodulation therapy to a patient's auditory cortex comprising evaluating a tinnitus pitch of the patient using a pitch matching method to determine a tinnitus center frequency; evaluating a tinnitus periodicity of the patient using a tinnitus periodicity estimation or determination method to determine a tinnitus periodicity; determining, for the patient, frequency and periodicity stimulation parameters corresponding to multiple therapeutic stimulation signals, where the frequency and periodicity parameters are calculated and generated on the basis of the patient's determined tinnitus pitch and tinnitus periodicity, the multiple therapeutic stimulation signals being configured to excite areas surrounding the center of tinnitus excitation in the patient's auditory cortex; and delivering to the patient the multiple therapeutic stimulation signals thereby to treat the patient's tinnitus.

Such a method may further comprise four separate therapeutic tones or signals, wherein each of the four therapeutic tones or signals has a unique combination of frequency and periodicity associated therewith; six separate therapeutic tones or signals, wherein each of the six therapeutic tones or signals has a unique combination of frequency and periodicity associated therewith; eight separate therapeutic tones or signals, wherein each of the eight therapeutic tones or signals has a unique combination of frequency and periodicity associated therewith; determining, for the patient, respective auditory filter bandwidths (AFBs) for each of the multiple therapeutic stimulation signals, each AFB having a respective width associated therewith; determining, for the patient, respective center frequencies for each of the multiple therapeutic stimulation signals; and determining, for the patient, respective intensities for each of the multiple therapeutic stimulation signals.

According to further embodiments, there is provided a system or device configured to deliver a two-dimensional acoustic coordinated reset neuromodulation therapy to a patient's auditory cortex comprising means for evaluating a tinnitus pitch of the patient using a pitch matching method to determine a tinnitus center frequency; means for evaluating a tinnitus periodicity of the patient using a tinnitus periodicity estimation or determination method to determine a tinnitus periodicity; means for determining, for the patient, frequency and periodicity stimulation parameters corresponding to multiple therapeutic stimulation signals, where the frequency and periodicity parameters are calculated and generated on the basis of the patient's determined tinnitus pitch and tinnitus periodicity, the multiple therapeutic stimulation signals being configured to excite areas surrounding the center of tinnitus excitation in the patient's auditory cortex, and means for delivering to the patient the multiple therapeutic stimulation signals thereby to treat the patient's tinnitus.

Such systems or devices may further comprise any one or more of four separate therapeutic tones or signals, wherein each of the four therapeutic tones or signals has a unique combination of frequency and periodicity associated therewith; six separate therapeutic tones or signals, wherein each of the six therapeutic tones or signals has a unique combination of frequency and periodicity associated therewith; eight separate therapeutic tones or signals, wherein each of the eight therapeutic tones or signals has a unique combination of frequency and periodicity associated therewith; means for determining respective auditory filter bandwidths (AFBs) for each of the multiple therapeutic stimulation signals, each AFB having a respective width associated therewith; and means for determining respective center frequencies for each of the multiple therapeutic stimulation signals; means for determining respective intensities for each of the multiple therapeutic stimulation signals.

The above-described embodiments should be considered as examples of the inventions described and disclosed herein, rather than as limiting the scope thereof. In addition to the foregoing embodiments, review of the detailed description and accompanying drawings will show that many other embodiments are contemplated that may not be explicitly disclosed or described herein. Accordingly, many combinations, permutations, variations and modifications of the foregoing embodiments will nevertheless fall within the spirit and scope of the various inventions described and disclosed herein. For example, implantable systems, devices and components may be adapted and configured for use in accordance with the teachings set forth herein, such as in cochlear implant devices and systems.

Although various methods and techniques have been described as being implemented in software, similar techniques can be implemented in hardware, firmware, or the like. Example hardware implementations include implementations within an application specific integrated circuit (ASIC), a field programmable gate array (FPGA), a programmable logic device, specifically designed hardware components, one or more processors, or any combination thereof. If implemented in software, a computer readable medium stores computer readable instructions, e.g., program code, that can be executed by a processor, DSP or other suitable computing device to carry out one of more of the techniques described above. For example, the computer readable medium can comprise random access memory (RAM), read-only memory (ROM), non-volatile random access memory (NVRAM), electrically erasable programmable read-only memory (EEPROM), flash memory, or the like. The computer readable medium can comprise computer readable instructions that when executed carry out one or more of the techniques described herein. The disclosed embodiments are presented for purposes of illustration and not limitation.

The invention claimed is:

1. A method of providing stimulation signals for acoustic coordinated reset neuromodulation therapy, the method comprising:
evaluating a tinnitus pitch and a tinnitus timbre to determine a set of tinnitus parameters comprising at least a tinnitus pitch parameter and a tinnitus timbre parameter;
determining at least one set of stimulation parameters based on the set of tinnitus parameters, wherein the at least one set of stimulation parameters comprises at least a stimulation pitch parameter and a stimulation timbre parameter;
generating at least one stimulation signal based on the determined at least one set of stimulation parameters.

2. The method according to claim 1, wherein the at least one set of stimulation parameters is determined based on the set of tinnitus parameters such that the stimulation pitch parameter and the stimulation timbre parameter are within a predetermined range relative to the tinnitus pitch parameter and the tinnitus timbre parameter.

3. The method according to claim 1, wherein determining at least one set of stimulation parameters based on the set of tinnitus parameters comprises:
defining a two-dimensional parameter space with the set of tinnitus parameters defining a tinnitus point in the two-dimensional space;

providing a maximum stimulation distance; and
determining the at least one set of stimulation parameters so that it defines a stimulation point in the two-dimensional space that is within the maximum stimulation distance from the tinnitus point.

4. The method according to claim 3, wherein determining at least one set of stimulation parameters based on the set of tinnitus parameters further comprises providing a minimum stimulation distance; and wherein the at least one set of stimulation parameters is determined so that the stimulation point in the two-dimensional space is spaced from the tinnitus point by at least the minimum stimulation distance.

5. The method according to claim 1, wherein determining at least one set of stimulation parameters comprises determining a plurality of sets of stimulation parameters based on the set of tinnitus parameters, each set of stimulation parameters comprising at least a stimulation pitch parameter and a stimulation timbre parameter; and wherein generating at least one stimulation signal comprises generating a plurality of stimulation signals, each stimulation signal being based on one of the determined sets of stimulation parameters.

6. The method according to claim 5, wherein the plurality of stimulation signals comprises three separate tones or signals, wherein each of the three tones or signals has a unique combination of frequency and periodicity associated therewith.

7. The method according to claim 5, further comprising determining, for a patient, respective intensities for each of the plurality of stimulation signals.

8. The method according to claim 5, wherein determining a plurality of sets of stimulation parameters based on the set of tinnitus parameters comprises:
defining a two-dimensional parameter space;
providing a minimum inter-signal distance; and
determining the plurality of sets of stimulation parameters so that each set of stimulation parameters defines a stimulation point in the two-dimensional space, wherein for each pair of stimulation points a distance between the stimulation points in the two-dimensional parameter space is at least the minimum inter-signal distance.

9. The method according to claim 8, wherein the plurality of sets of stimulation parameters comprises at least three sets of stimulation parameters, and the respective stimulation points in the two-dimensional parameter space form a polygon such that a tinnitus point defined in the two-dimensional parameter space by the set of tinnitus parameters is within said polygon.

10. The method according to claim 1, wherein evaluating a tinnitus pitch and a tinnitus timbre to determine a set of tinnitus parameters comprises:
determining as the tinnitus pitch parameter a fundamental frequency $f_T$ of a tinnitus experienced by a patient;
generating a timbre evaluation signal based on a combination of a first and a second evaluation signal with a tunable relative strength of the first and the second evaluation signal, wherein the first evaluation signal comprises a frequency corresponding to the determined tinnitus pitch parameter, and the second evaluation signal comprises at least one frequency outside a predetermined fundamental frequency bandwidth around the frequency corresponding to the determined tinnitus pitch parameter;
receiving the patient's selection for a setting of the tunable relative strength; and
determining the tinnitus timbre parameter based on the patient's selection.

11. The method according to claim 10, wherein the predetermined fundamental frequency bandwidth extends from about $0.5*f_T$ to about $2*f_T$.

12. The method according to claim 10, wherein the determined tinnitus timbre parameter defines a ratio of a power of frequency components in a tinnitus evaluation signal outside the predetermined fundamental frequency bandwidth relative to an overall power of the tinnitus evaluation signal.

13. The method according to claim 1, wherein the at least one stimulation signal is generated based on a combination of a first and a second stimulation signal component with a relative strength of the first and the second stimulation signal component determined by the stimulation timbre parameter, wherein the first stimulation signal component comprises a frequency determined by the stimulation pitch parameter, and the second stimulation signal component comprises at least one frequency outside a predetermined fundamental stimulation frequency bandwidth around the frequency determined by the stimulation pitch parameter, wherein a relative intensity of the second stimulation signal component is determined by the stimulation timbre parameter.

14. A system or device configured to provide/deliver stimulation signals for acoustic coordinated reset neuromodulation therapy, the system comprising:
means for evaluating a tinnitus pitch and a tinnitus timbre to determine a set of tinnitus parameters comprising at least a tinnitus pitch parameter and a tinnitus timbre parameter;
means for determining at least one set of stimulation parameters based on the set of tinnitus parameters, wherein the at least one set of stimulation parameters comprises at least a stimulation pitch parameter and a stimulation timbre parameter;
means for generating at least one stimulation signal based on the determined at least one set of stimulation parameters.

15. A computer program product comprising computer readable code, which when loaded and executed by a computer system, causes the computer system to:
evaluate a tinnitus pitch and a tinnitus timbre to determine a set of tinnitus parameters comprising at least a tinnitus pitch parameter and a tinnitus timbre parameter;
determine at least one set of stimulation parameters based on the set of tinnitus parameters, wherein the at least one set of stimulation parameters comprises at least a stimulation pitch parameter and a stimulation timbre parameter; and
generate at least one stimulation signal based on the determined at least one set of stimulation parameters.

16. The computer program product according to claim 15, wherein the at least one set of stimulation parameters is determined based on the set of tinnitus parameters such that the stimulation pitch parameter and the stimulation timbre parameter are within a predetermined range relative to the tinnitus pitch parameter and the tinnitus timbre parameter.

17. The computer program product according to claim 15, wherein the computer readable code causes the computer system to determine at least one set of stimulation parameters based on the set of tinnitus parameters by:
defining a two-dimensional parameter space with the set of tinnitus parameters defining a tinnitus point in the two-dimensional space;
providing a maximum stimulation distance; and
determining the at least one set of stimulation parameters so that it defines a stimulation point in the two-dimensional space that is within the maximum stimulation distance from the tinnitus point.

18. The computer program product according to claim 17, wherein executing the computer readable code causes the computer system to determine at least one set of stimulation parameters based on the set of tinnitus parameters by further by providing a minimum stimulation distance; and wherein the at least one set of stimulation parameters is determined so that the stimulation point in the two-dimensional space is spaced from the tinnitus point by at least the minimum stimulation distance.

19. The computer program product according to claim 15, wherein executing the computer readable code causes the computer system to determine the at least one set of stimulation parameters by determining a plurality of sets of stimulation parameters based on the set of tinnitus parameters, each set of stimulation parameters comprising at least a stimulation pitch parameter and a stimulation timbre parameter; and wherein the computer system generates at least one stimulation signal by generating a plurality of stimulation signals, each stimulation signal being based on one of the determined sets of stimulation parameters.

20. The computer program product according to claim 19, wherein the plurality of stimulation signals comprises three separate tones or signals, wherein each of the three tones or signals has a unique combination of frequency and periodicity associated therewith.

\* \* \* \* \*